(12) United States Patent
Nardo et al.

(10) Patent No.: US 7,977,099 B2
(45) Date of Patent: Jul. 12, 2011

(54) METHOD FOR ALCOHOL CONTENT DETERMINATION

(75) Inventors: Oscar Nardo, Padua (IT); Martino Nardo, Cumberland, RI (US); Piero Franco, Cumberland, RI (US)

(73) Assignee: Hanna Instruments, Inc., Woonsocket, RI (US)

( * ) Notice: Subject to any disclaimer, the term of this patent is extended or adjusted under 35 U.S.C. 154(b) by 532 days.

(21) Appl. No.: 12/192,624

(22) Filed: Aug. 15, 2008

(65) Prior Publication Data

US 2009/0048786 A1    Feb. 19, 2009

Related U.S. Application Data

(60) Provisional application No. 60/955,901, filed on Aug. 15, 2007.

(51) Int. Cl.
*G01N 33/14*    (2006.01)
*G01N 27/06*    (2006.01)

(52) U.S. Cl. ........ 436/24; 422/68.1; 422/82.01; 436/20; 436/131; 436/132; 436/149; 436/150

(58) Field of Classification Search ................ 422/68.1, 422/82.01; 436/20, 24, 131–132, 149–151
See application file for complete search history.

(56) References Cited

U.S. PATENT DOCUMENTS

| | | | |
|---|---|---|---|
| 3,838,971 A | 10/1974 | Albertson | |
| 3,877,291 A | 4/1975 | Hoppesch et al. | |
| 4,209,299 A * | 6/1980 | Carlson | 436/150 |
| 4,323,004 A | 4/1982 | Sereda et al. | |
| 5,033,293 A | 7/1991 | Homma et al. | |
| 5,182,523 A | 1/1993 | Ertel et al. | |
| 5,318,078 A | 6/1994 | Hantmann | |
| 5,488,311 A | 1/1996 | Kamioka et al. | |
| 6,030,839 A | 2/2000 | Yamamoto et al. | |
| 6,542,828 B2 | 4/2003 | MacDonald et al. | |
| 6,920,399 B2 | 7/2005 | Priev et al. | |
| 2006/0042940 A1* | 3/2006 | Kawanishi et al. | 204/403.01 |

FOREIGN PATENT DOCUMENTS

| | | |
|---|---|---|
| DE | 19948465 A | 10/1999 |
| JP | 2003004684 A | 6/2001 |

OTHER PUBLICATIONS

Svetlicic V. et al, Chemistry of Materials 1998, 10, 3305-3307.*
Lopes, A. et al, Journal of Solution Chemistry 1999, 28, 117-131.*
Colombie, S. et al, Journal of Bioscience and Bioengineering 2007,103, 229-235.*

* cited by examiner

*Primary Examiner* — Arlen Soderquist
(74) *Attorney, Agent, or Firm* — Barlow, Josephs & Holmes, Ltd.

(57) ABSTRACT

The present invention provides a low-cost, easy-to-use, and accurate method and apparatus for determining alcohol content in a test sample, such as wine. The method for alcohol content determination includes the following steps. A known quantity of a test sample is provided. A measurement of electrolytic conductivity EC0 of the test sample is taken. Next, a known quantity of conductive additive with known composition is added to the test sample to produce a first solution. A measurement of Electrolytic conductivity EC1 is taken for the first solution. Data representing predetermined values for EC0 and EC1 with corresponding known alcohol concentrations is provided for comparison. The electrolytic conductivity values for EC0 and EC1 are cross-referenced against the known data to determine a value for the alcohol concentration of the test sample. In addition, the values for EC0 and EC1 are adjusted for temperature and other variables.

29 Claims, 14 Drawing Sheets

METHOD FOR ALCOHOL CONTENT DETERMINATION

CROSS-REFERENCE TO RELATED APPLICATION

This application is related to and claims priority from earlier filed provisional patent application Ser. No. 60/955,901, filed Aug. 15, 2007 which is incorporated herein by reference.

BACKGROUND OF THE INVENTION

The present invention generally relates to a method for determining alcohol content in vapor and liquids. More specifically, the present invention relates to a method that compares electrolytic conductivity of an alcohol-containing solution with and without a conductive additive for mapping to a data field for generation of an alcohol concentration value.

The alcoholic beverage industries (wine, beer, spirits, malt-based beverages, etc.), require an accurate measurement of alcohol content for both regulatory and sensory purposes. Many established measurement techniques and instrumentations are produced for this purpose. For example, NIR spectroscopy, gas chromatography, and FTIR spectroscopy are used to measure alcohol content but are very expensive and require thoroughly trained scientific personnel to properly analyze and maintain the instrumentation. Other techniques used for measurement of alcohol content include an ebulliometer, distillation, catalytic combustion and enzymatic reactions. These techniques may have errors due to barometric pressure, sugar content, volatiles, and acids.

Electrolytic conductivity has been used to determine concentration of ionic substances in binary solutions. Electrolytic conductivity is considered a nonselective technique, however, under certain conditions it has been used for specific substrate evaluation. The patents discussed below illustrate specific examples.

U.S. Pat. No. 6,030,839, issued to Yamamoto et al., shows a method for determining sodium concentration in alcohol comprising the steps of: (a) preparing a characteristic curve of conductivity showing the relationship between sodium concentration in alcohol and conductivity of alcohol as observed at a predetermined temperature and a temperature correction curve showing the change in conductivity per unit degree centigrade of alcohol temperature versus sodium concentration in alcohol; (b) measuring the conductivity and temperature of a sample alcohol simultaneously; (c) subjecting the measured conductivity to temperature correction according to the temperature correction curve; and (d) determining the sodium concentration in the sample alcohol on the basis of the corrected conductivity thus obtained (See Abstract and claim 1).

U.S. Pat. No. 6,542,828, issued to MacDonald, shows a method of determining the concentration of an acid or base in an stripping alcohol solution comprising the steps of: (a) measuring a first electrolytic conductivity value for the solution and a second electrolytic conductivity value for the solution, where the first physical property and the second physical property can be respectively defined in the form of a first solution property equation and a second solution property equation, in which, each equation expresses the respective physical property as a function of the concentration of one of the acids or bases; (b) inserting the measured values into the respective solution property equations; and (c) solving the solution property equations simultaneously (See claim 1, 31 and Col. 2, line 26 to Col. 3, line 53). This invention is of interest because it illustrates the use of a database of values that correlate a given concentration of material to a given physical property value, such as electrolytic conductivity. When the electrolytic conductivity is determined, the concentration of the material can be determined.

U.S. Pat. No. 6,920,399, issued to Priev, shows a method for analyzing a fluid to obtain the concentrations of a number of mineral salts of the fluid components comprising the steps of: (a) bringing a sample of the fluid to a plurality of successive temperatures; (b) measuring N electrolytic conductivity parameters of the sample at each temperature; and (c) determining simultaneously the concentrations of N components of the fluid using the conductivity parameters (claim 1 and 9).

Japanese Patent Number JP2003004684 shows a method of determining alcohol content in an ink composition by measuring the electrolytic conductivity of water-based ink (See Abstract). As in paragraph [014], a conductivity-alcoholic concentration conversion table is used from recorded data. When a given electrolytic conductivity is sensed, the corresponding alcohol content can be determined.

The patents discussed above utilize techniques to determine the concentration of a substrate including that of alcohol in a mixture. Although instrumentation is available for alcohol measurements, either trained personnel, considerable expense, timely calibrations, barometric pressure error, sugar content error, and subjective determinations are their short comings. The prior art does not satisfy the need for a low cost, reliably accurate, easy to use method for determination of alcohol content in a vapor or liquid.

In view of the foregoing, there is a desire for a method for alcohol content determination that effectively determines the content of alcohol by measuring electrolytic conductivity. It is also desirable to provide a method that will verify the measurement of electrolytic conductivity. It is also desirable to have a method that requires minimal user experience and less time to calculate the alcohol content of a liquid. It is also desirable to provide a method for alcohol content determination that costs substantially less than currently available methods.

SUMMARY OF THE INVENTION

The present invention preserves the advantages of prior methods for determining alcohol content. In addition, it provides new advantages not found in currently available methods for determining alcohol content and overcomes many disadvantages of such currently available methods for determining alcohol content.

The present invention provides a method that determines the alcohol content by measuring the electrolytic conductivity of a liquid solution and the electrolytic conductivity of the liquid solution with a conductive additive added thereto. The content of alcohol in a liquid as a function of its electrolytic conductivity after a conductive additive is added to the liquid is a predetermined value. When it is added to the liquid under test (e.g. wine), the conductivity of the entire liquid solution with the conductive additive will change. A number of alcohol concentration curves have been developed from extensive testing which produced actual data. These data curves are developed from knowing the initial conductivity EC0 and conductivity after the conductive additive is added EC1. Each of the curves, as a result, correspond to an alcohol content percentage in a liquid solution and are used as a databank for later comparing results of actual testing values.

In operation, for testing a liquid with an unknown amount of alcohol, a user provides a known quantity Vs of a test sample. Next, the initial electrolytic conductivity EC0 and temperature T0 of the test sample is measured before the first conductive additive is added. Measurement of temperature is not required although it makes the test more accurate. Then a known quantity V1 of a first conductive additive with known composition is added to produce a first solution. After adding the first conductive additive, the electrolytic conductivity EC1 and temperature T1 is measured again to arrive at an EC1 conductivity value. To determine the conductivity of the liquid, data, such as a graph, that represents predetermined values having an x axis for EC0 and y axis for EC1 with corresponding curves plotting known alcohol concentrations are used. The measured value for EC0 is found on the x axis of a graph and a vertical line is drawn upwards so it crosses the different alcohol concentration curves. The measured EC1 value is found on the y axis and a horizontal line is drawn to the right until it crosses the vertical line from EC0. The intersection of the two points will fall on one of the curves. It is this intersected curve that determines which alcohol percentage is found in the liquid under test. Of course, if the intersection of EC0 and EC1 is between curves, the alcohol content can be extrapolated. In addition, a compensation factor is added to the value for the alcohol concentration to adjust for sugar and temperature to provide an adjusted alcohol concentration. To validate the results, a second electrolytic conductivity EC2 can be measured by an addition of a second conductive additive to derive a second alcohol concentration for comparison to the first alcohol concentration. Note, this method is also capable of being implemented in a software algorithm to generate and reproduce the needed data.

It is therefore an object of the present method for determining alcohol content to provide a low cost and accurate method.

It is a further object of the method for determining alcohol content to provide a short analysis time and minimal sample preparation.

It is a further object of the method for determining alcohol content to provide infrequent calibration.

Yet another object is to provide a method for determining alcohol content in many different types of liquids.

Another object of method for determining alcohol content is to provide a non-toxic process for use by inexperienced users which works at different temperatures and sugar concentrations.

BRIEF DESCRIPTION OF THE DRAWINGS

The novel features which are characteristic of the method for alcohol content determination are set forth in the appended claims. However, the method for alcohol content determination, together with further embodiments and attendant advantages, will be best understood by reference to the following detailed description taken in connection with the accompanying drawings in which:

DETAILED DESCRIPTION OF THE PREFERRED EMBODIMENTS

The present method solves the problems in method for alcohol content determinations by providing a new and unique method for determining alcohol content accurately and inexpensively. Generally, the present method is a method for alcohol content determination in liquid or vapor. More specifically, the present method provides a method for alcohol content determination used to determine percentage of alcohol in alcoholic beverages such as wine, beer, spirits, or malt-based beverages.

Figure 1A:
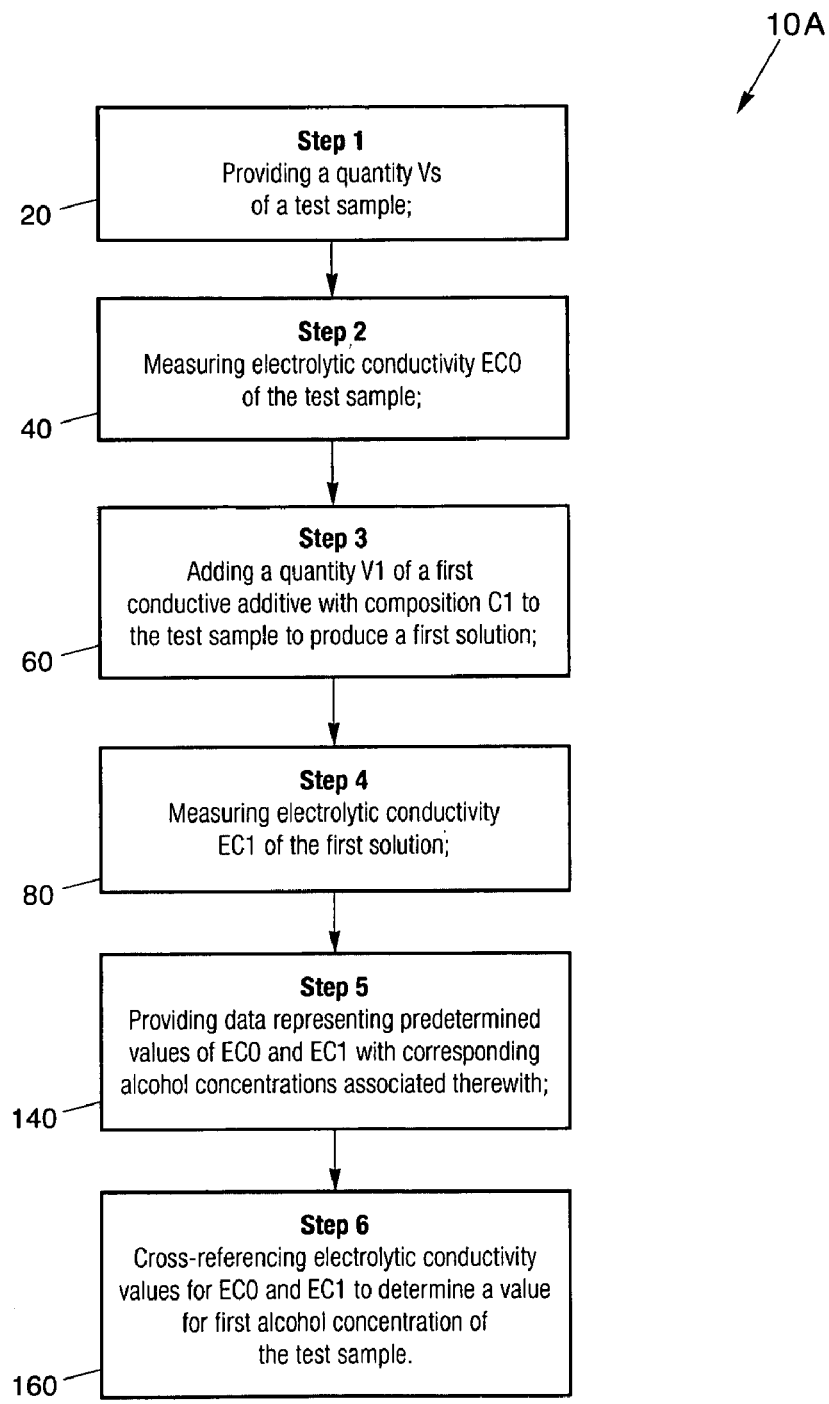
FIG. 1A is a flow chart for a method for alcohol content determination of the present invention.
Figure 1B:
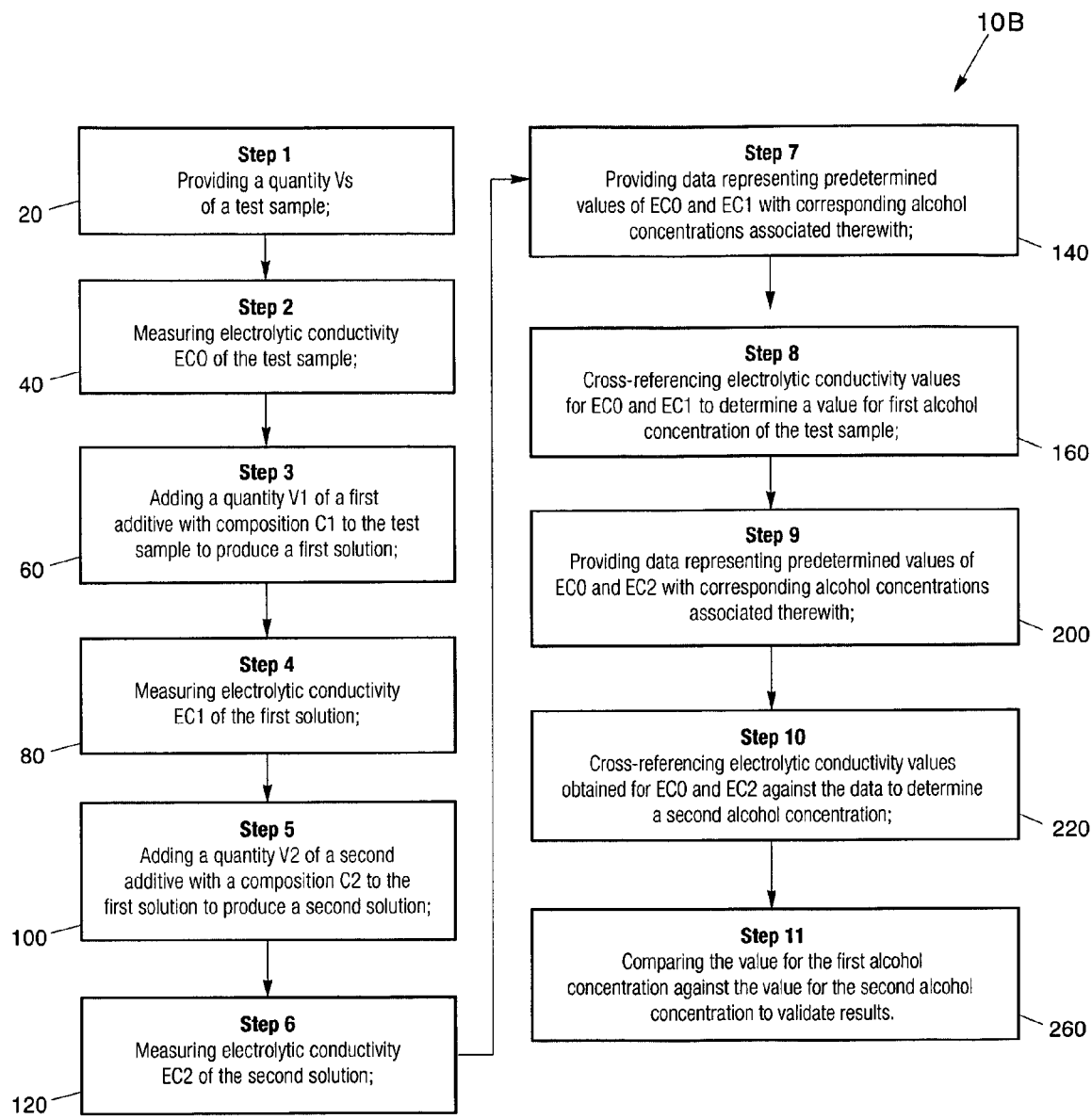
FIG. 1B is a flow chart of FIG. 1A that includes a second alcohol concentration to validate the first alcohol concentration.
Figure 1C:
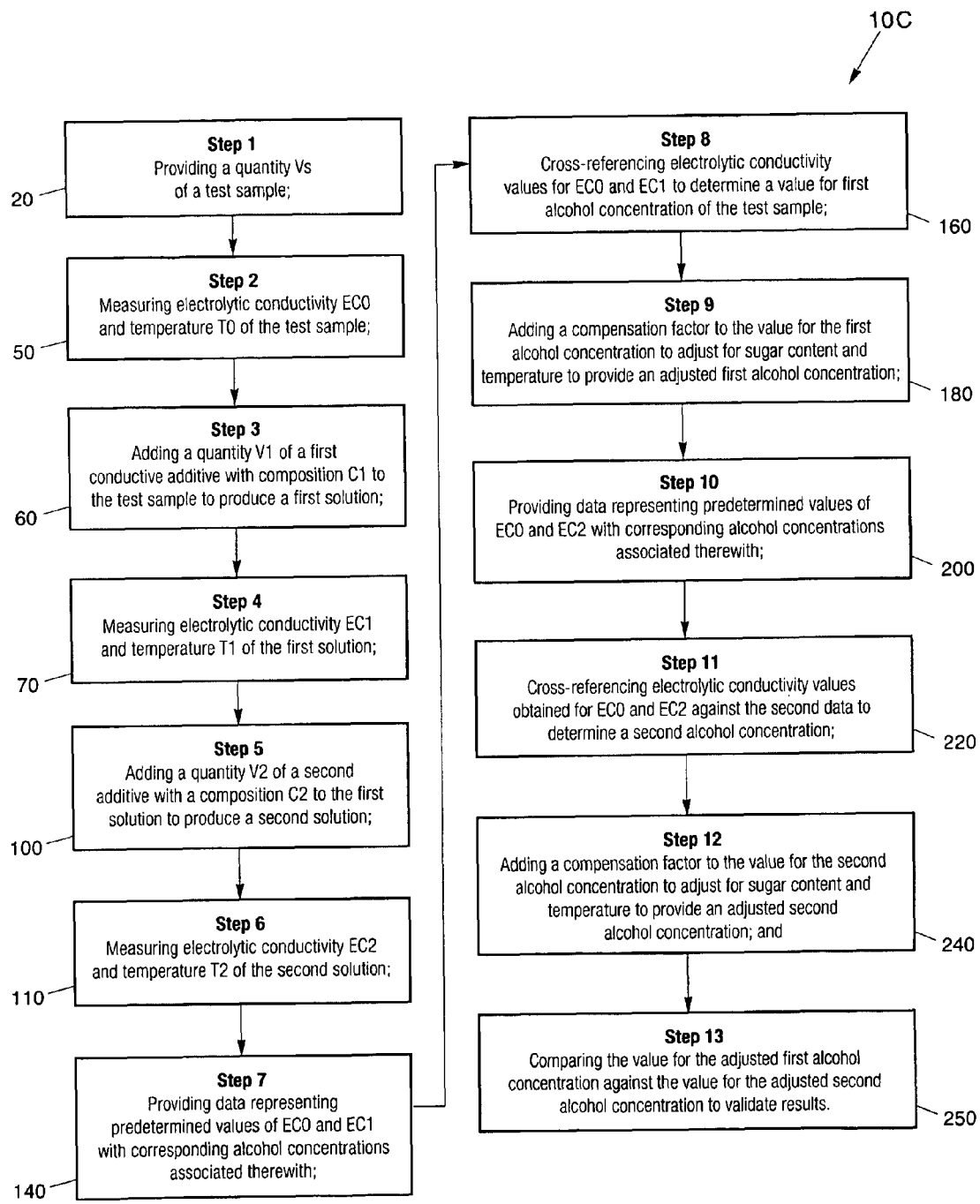
FIG. 1C is a flow chart of FIG. 1B that includes compensation factors for sugar content and temperature to increase the accuracy of the alcohol concentration.

Now referring to FIGS. 1A-1C, the method for alcohol content determination (10A, 10B, 10C) of a test sample is illustrated in a flow chart. Generally, the method for alcohol content determination measures the change in electrolytic conductivity of a solution as a function of the content of alcohol in the solution and any additions to the solution. The method of alcohol content determination 10A, as shown in FIG. 1A, is the six primary steps for performing the method for alcohol content determination.

Another embodiment of the method of alcohol content determination 10B, as shown in FIG. 1B, the method 10B includes the six primary steps from method 10A plus it provides additional steps for a second alcohol concentration to validate the first alcohol concentration. In another embodiment of the method of alcohol content determination 10C, as shown in FIG. 1C, the method 10C includes the steps from method 10B plus it provides compensation factors for temperature and sugar to increase the accuracy of the results. It should be noted that the method of the present invention may include more than or fewer than the steps outlined in methods 10A-10C of FIGS. 1A-1C.

For purposes of explanation, the steps for method 10C are discussed below which incorporates the steps outlined in both the method 10A and method 10B. The first step of the method of alcohol content determination 10C is providing a known quantity of the liquid to be tested, known as a test sample 20. The known quantity of the test sample is labeled as Vs. In one embodiment, the Vs is 60 mL and the test sample is wine. Of course, it is contemplated that a test sample may be any liquid solution or alcoholic beverage for determination of alcohol content. For example, the alcoholic beverage may be beer, wine, or spirits. In addition, the Vs may be greater than or less than 60 mL.

The second step of the method of alcohol content determination 10C is measuring initial electrolytic conductivity EC0 of the test sample 40. By way of background, electrolytic conductivity is a measure of a test sample's ability to conduct an electrical current. When an electrical potential difference is placed across the test sample, its movable charges flow, giving rise to an electric current. In the prior art, it is known to use an electrical conductivity meter to measure conductivity in a solution. For the present method, an apparatus 500, discussed further herein, is used to measure the electrical conductivity of the solution. The conductivity readings are obtained using standard precautions (e.g. stirring). Optionally, at this step, the temperature T0 may also be measured 50. The temperature reading T0 obtained may be adjusted to equate with temperatures used in a graph with known alcohol concentrations. The temperature reading T0 is obtained to produce a compensation factor which is discussed further below.

The third step for the method of alcohol content determination 10C is adding a known quantity of a conductive additive V1 with known composition C1 to the test sample to produce a first solution 60. In one embodiment, the conductive additive is KCl (potassium chloride) and the quantity of the additive V1 is equal to 30 mL. It should be noted that alternative conductive additives, other than potassium chloride, may be used which are capable of conducting electricity. Generally, any conductive salt may be suitable as a conductive additive for use in the present method. For example, NaCl, KNO3, and LiCl may be used in the present method. Also, it should be noted that variable quantity of conductive additive may be used other than the quantities disclosed herein.

The fourth step for the method of alcohol content determination 10C is measuring electrolytic conductivity EC1 of the first solution 80. By measuring the value for electrolytic conductivity EC1 with a first conductive additive having a known composition C1, such as KCl, and comparing that value against EC0 without a conductive additive, it provides a more accurate reading of the alcohol content. Optionally, at this step, the temperature T1 may also be measured 70. The temperature reading T1 obtained may be adjusted to equate with temperatures used in a graph with known alcohol concentrations. The temperature reading T0 is obtained to produce a compensation factor which is discussed further below.

To increase the accuracy of the results, the fifth step for the method for alcohol content determination 10C may be used. The fifth step is adding a known quantity V2 of a second conductive additive with a known composition C2 to the first solution to produce a second solution 100. In one embodiment, the second conductive additive is KCl (potassium chloride) and the quantity of the additive (V2) is equal to 30 mL. Alternatively, the second conductive additive may be something other than potassium chloride. Also, the second conductive additive may be the same or different from the first conductive additive to validate the results.

The sixth step for the method of alcohol content determination 10C is measuring electrolytic conductivity EC2 of the second solution 120. EC2 is being used as a second test of electrolytic conductivity to validate the results obtained in EC1 and EC0 for alcohol content in a liquid solution. Alternatively, at this step, the temperature T2 may also be measured 110. The temperature reading T2 obtained may be adjusted to equate with temperatures used in a graph with known alcohol concentrations. The temperature reading T2 is obtained to produce a compensation factor which is discussed further below.

Figure 2:
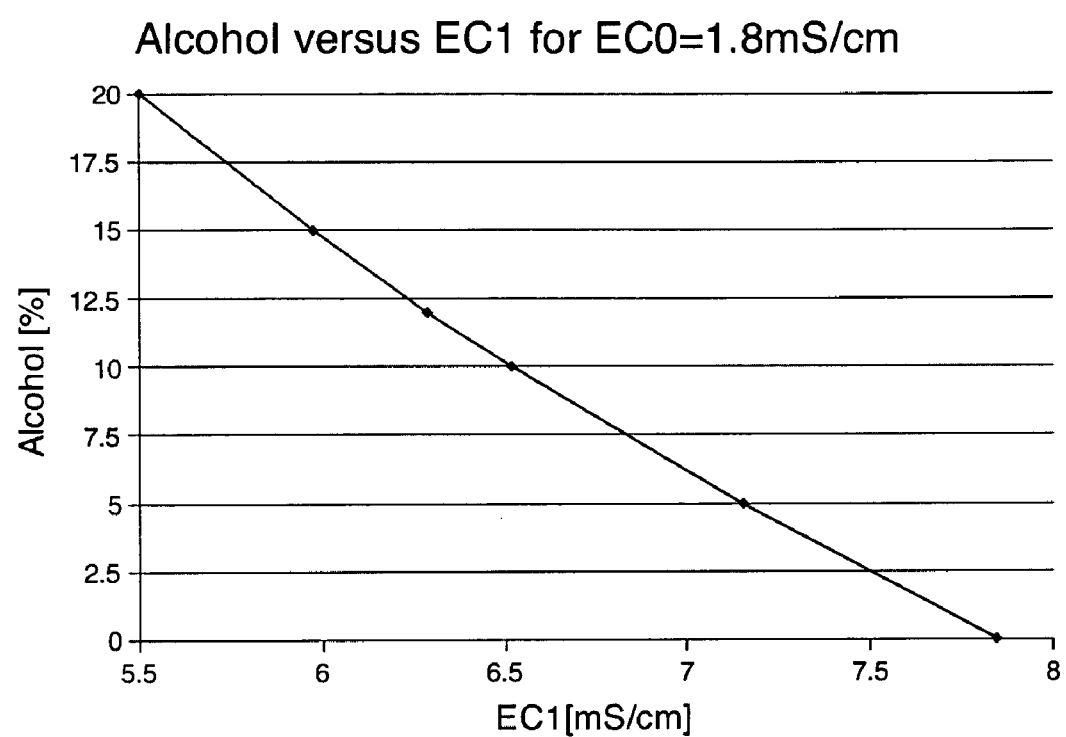
FIG. 2 is a graph of sample data for use with the method for alcohol content determination in FIGS. 1A-1C with an x axis of EC1 mS/cm for electrolytic conductivity of a solution with a conductive additive and a y axis of alcohol percentage by volume.

Now referring to FIG. 2, for one test sample, an alcohol concentration curve is plotted along a graph based upon six standard solutions of alcohol, water and a conductive additive, such as KCl, and were made with the same initial conductivity EC0 of 1.8 (mS/cm) and different alcohol percentages by volume (0%, 5%, 10%, 12%, 15% and 20%). With regard to wine, it is contemplated that the plotted curve may range in alcohol percentage anywhere between 0% to 25% with higher accuracy occurring between 10-15%. Sample data as illustrated in the graph of FIG. 2, shows the change in conductivity for standard solutions when 30 mL of 1M KCl (conductive additive) was added to each solution. In FIG. 2, an alcohol concentration curve was plotted using an initial conductivity (EC0) of 1.8 (mS/cm). The electrolytic conductivity after the addition (EC1) depends on the quantity of alcohol solution. By measuring EC1 of a liquid solution, the quantity of alcohol by volume can be determined. The relationship between alcohol content by volume and electrolytic conductivity (EC1) is almost linear.

Figure 3:
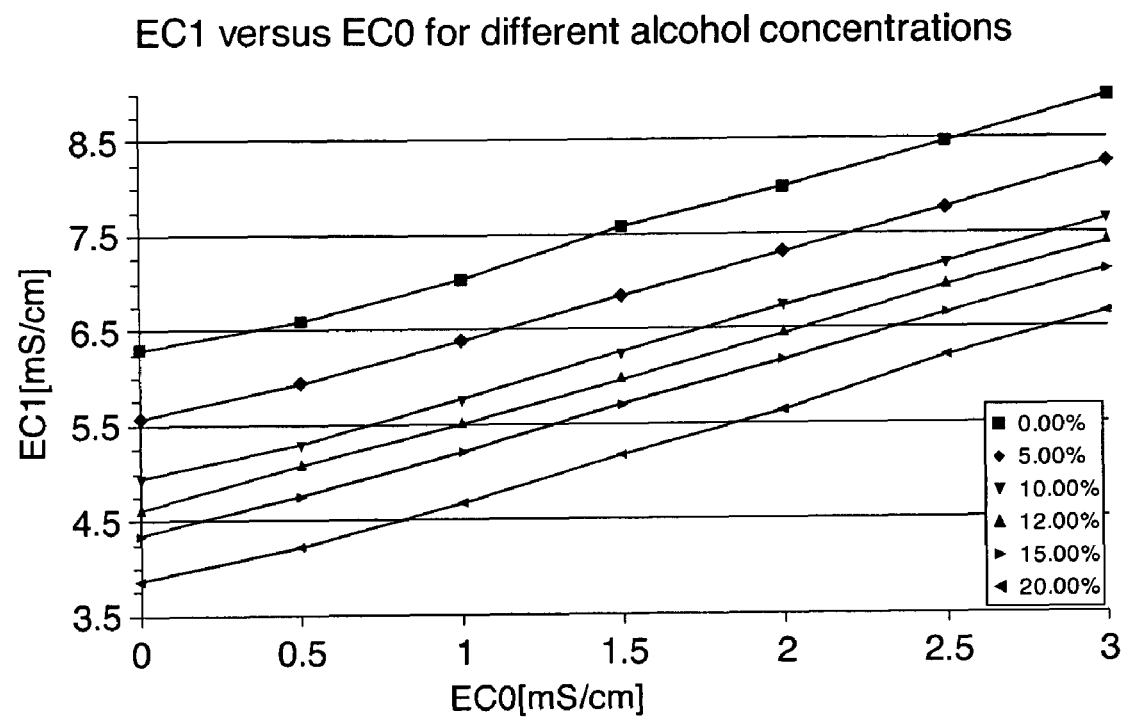
FIG. 3 is a graph for use with the method for alcohol content determination in FIGS. 1A-1C with an x axis of EC0 mS/cm for electrolytic conductivity of a test sample and a y axis of EC1 mS/cm for electrolytic conductivity of the test sample with a conductive additive having multiple lines representing different alcohol percentages in the sample (0%, 5%, 10% 12%, 15%, 20%)

The seventh step for the method of alcohol content determination 10C is providing a first graph representing predetermined values having an x axis for EC0 and a y axis for EC1 with corresponding curves plotting known alcohol concentrations 140. The graph of FIG. 3 shows the conductivity EC1 and EC0 after one addition for standard solutions with known alcohol content and different initial conductivities. The graph of FIG. 3 plots an alcohol concentration curve based upon different alcohol concentrations (0%, 5%, 10%, 12%, 15%, 20%) as a function of EC1 (y axis) and EC0 (x axis). Using FIG. 3, the quantity of alcohol can be determined for test samples of any initial conductivity. In addition, different temperatures can be used to allow testing of test samples with different temperatures. Corresponding curves were obtained for multiple initial conductivities in the range of 0 to 3 (mS/cm). The procedure can be extended to higher ranges if necessary.

It should be noted that the graphs of FIGS. 2 and 3 represent sample data to illustrate the present invention. Different data, using different curves may be used and still be within the scope of the present invention.

The eighth step for the method of alcohol content determination 10C is cross-referencing electrolytic conductivity values for EC0 and EC1 against a first graph, as shown in FIG. 3, to determine a value for the first alcohol concentration of the test sample 160. The EC0 value and EC1 value intersect on the curved alcohol concentration line. The value listed on the alcohol concentration line is the equivalent alcohol concentration percentage. If the intersection point does not fall on the curved alcohol concentration line, the percentage of alcohol is extrapolated. For example, if EC1 is 7.5 mS/cm and EC0 is 1.5 mS/cm, then the alcohol content by volume is approximately 0%. Another example, if EC1 is 6.5 mS/cm and EC0 is 2 mS/cm, and then the alcohol content by volume is approximately 12%.

The ninth step for the method of alcohol content determination 10C is adding compensation factors to the value for the alcohol concentration to provide an adjusted first alcohol concentration 180. Due to quantities of other components in alcoholic beverages apart from water and alcohol, a compensation factor is preferably added to the value for alcohol content. To provide a more accurate measurement, a compensation factor is added to the value for alcohol concentration to adjust for additional variables such as sugar content or temperature in the test sample.

It is well known in the art that electrical conductivity depends on temperature and therefore a temperature compensation factor is used. Temperature is preferably factored in for more accurate measurement results. Temperature is a variable that maybe selected from one of the following: automatic temperature compensation (preset temperature adjustment) if desired, no temperature compensation, and manual temperature compensation if desired. It should be noted that the temperature range for wine is typically from 5 to 35° C. with high accuracy between 15-20° C.

Another compensation factor is sugar. Generally, to identify the sugar content of the sample, and therefore calculate the sugar compensation factor, the sugar content of the test sample is labeled either fixed, type, or content. When the sugar is "fixed", the sugar content is unknown. When the sugar is "type", the type of test sample is known. When the sugar is "content", the amount of sugar in the test sample is known.

For example, when "fixed" is the sugar content for wine, the sugar content is unknown and defers to a default sugar compensation factor. The "fixed" usually occurs for dry and medium-dry wines (sugar content less than 12 mg/L). With wine, sugar content over 12 mg/L affects the accuracy of the alcohol content value. When "content" is selected, the amount of sugar in wine is known. When "content" is selected, the amount of sugar in wine is known and provided manually by user.

It should be noted that in order of preference, content would be most preferable, fixed would be next, and type would be last. Where content provides a more accurate measurement of sugar compensation and type would provide the least accurate measurement of sugar compensation of the three.

When "type" is selected for sugar compensation, the wine type is known. Wine type is available when type is selected as the sugar compensation method and is used to select the wine type. With regard to wine, the options for wine type are: dry, meddry (medium-dry), medsweet, or sweet. The dry wine has sugar content ranging from 0 to 1.4 g/L. The meddry (medium-dry) wine has sugar content ranging from 1.4 to 4.12 g/L. The medsweet (medium-sweet) wine has sugar content ranging from g/L to 12.45 g/L. The sweet wine has sugar content ranging from 12.45 g/L to 45 g/L. Note, the sugar compensation factor can be applied to any liquid or any alcoholic beverage, similar to wine, by adjusting accordingly the sugar compensation.

To evaluate the EC1 differences between the wine samples and corresponding standard alcohol samples from different wine categories (dry, medium-dry, medium-sweet, sweet) were measured. The EC0 and EC1 conductivity values were measured at 25° C. using a measuring method. The measuring method involves a volumetric addition using a pipette and a titrator. The EC1 conductivity value for each wine sample was compared with the EC1 conductivity value measured for alcohol standard with the same alcohol content similar to the wine sample with the same initial conductivity EC0 at 25° C. In this way, an alcohol-wine difference factor was obtained for each wine.

From the results of the three types of sugar compensation, the alcohol-wine difference factor was determined. When the sugar content is "fixed", the mean value of all factors for dry and medium-dry wines is used. When the sugar content is "type", the mean value for each family of wines: dry, medium-dry, and medium-sweet is used. When the sugar content is "content", a linear regression function calculates the compensation factor based on the quantity of sugar entered by the user. Regardless of sugar compensation method used, the alcohol-wine difference factor is used by adding its value to the measured EC1 conductivity value.

Figure 4:
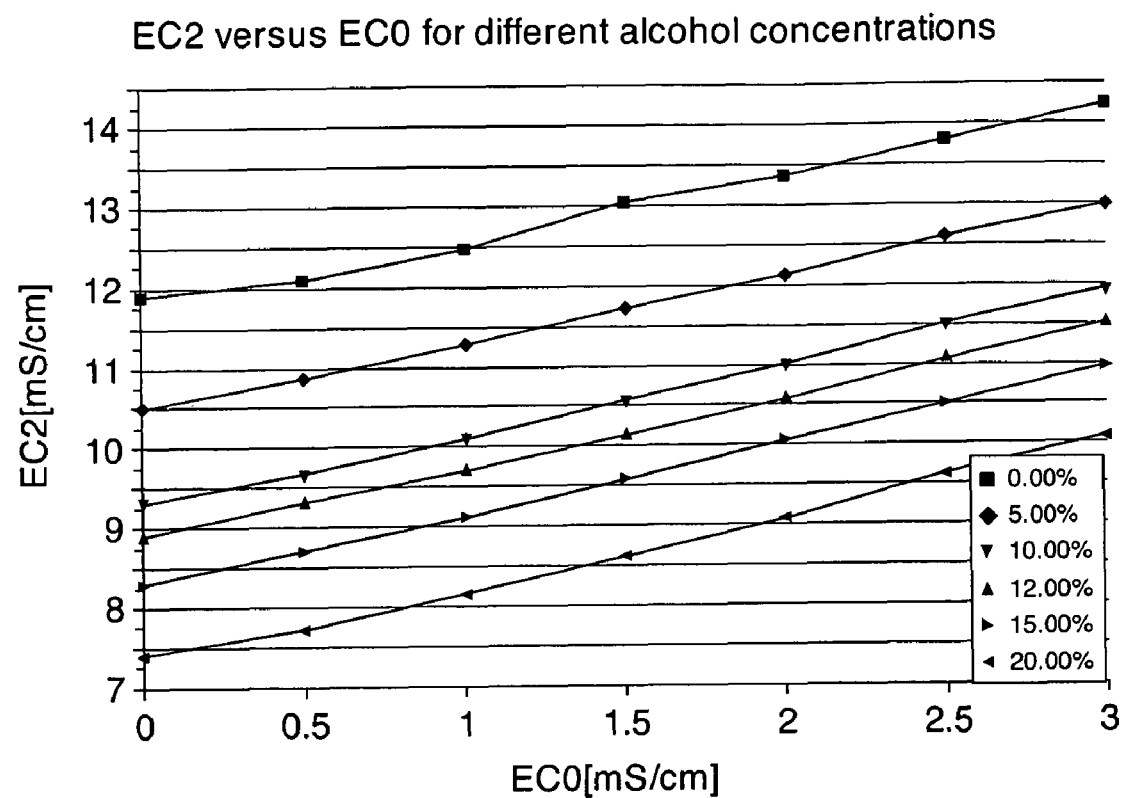
FIG. 4 is a graph for use with the method for alcohol content determination in FIGS. 1A-1C with an x axis of EC0 mS/cm for electrolytic conductivity of a test sample and a y axis of EC2 mS/cm for electrolytic conductivity of the test sample with two conductive additives having multiple lines representing different alcohol percentages (0%, 5%, 10% 12%, 15%, 20%)

Now referring to FIG. 4, the tenth step for the method of alcohol content determination of 10C is providing a graph representing predetermined values having an x for EC0 and y axis for EC2 with corresponding curves plotting known alcohol concentrations 200. The graph shows the conductivity of EC2 and EC0 after a second addition for standard solutions with known alcohol content and different initial conductivities. The graph plots an alcohol concentration curve based upon different alcohol concentrations (0%, 5%, 10%, 12%, 15%, 20%) as a function of EC2 (y axis) and EC0 (x axis). Using FIG. 4, the quantity of alcohol can be determined for test samples of any initial conductivity. In addition, different temperatures can be used to allow testing of test samples with different temperatures.

The eleventh step for the method of alcohol content determination 10C is cross-referencing electrolytic conductivity values for EC0 and EC2 against the second graph to determine a value for the second alcohol concentration of the test sample 220. Referring to FIG. 4, the EC0 value and EC2 value intersect on the second graph at a curved alcohol concentration line. The value listed on the alcohol concentration line is the equivalent alcohol concentration percentage. If the intersection point does not fall on the curved alcohol concentration line, the percentage of alcohol is extrapolated.

The twelfth step for the method of alcohol content determination 10C is adding a compensation factor to the value for the second alcohol concentration to provide an adjusted second alcohol concentration 240. The adjustment factor would include sugar compensation, such as type of test sample, or temperature T2 in calculating the proper adjustment.

The thirteenth step for the method of alcohol content determination 10C is comparing the value for the adjusted first alcohol concentration against the value for the adjusted second alcohol concentration to validate values 250. It should be noted that at least one conductive additive may be used for determining an alcohol concentration to determine alcohol content. The second conductive additive is used to increase the accuracy and to validate that additions were correctly performed. Similarly, three or more conductive additives may be used to further increase the accuracy and validation of the alcohol content. Also, in the examples above, the conductive additives may be performed sequentially or each additive can be done on different volumes of the original sample.

Figure 5A:
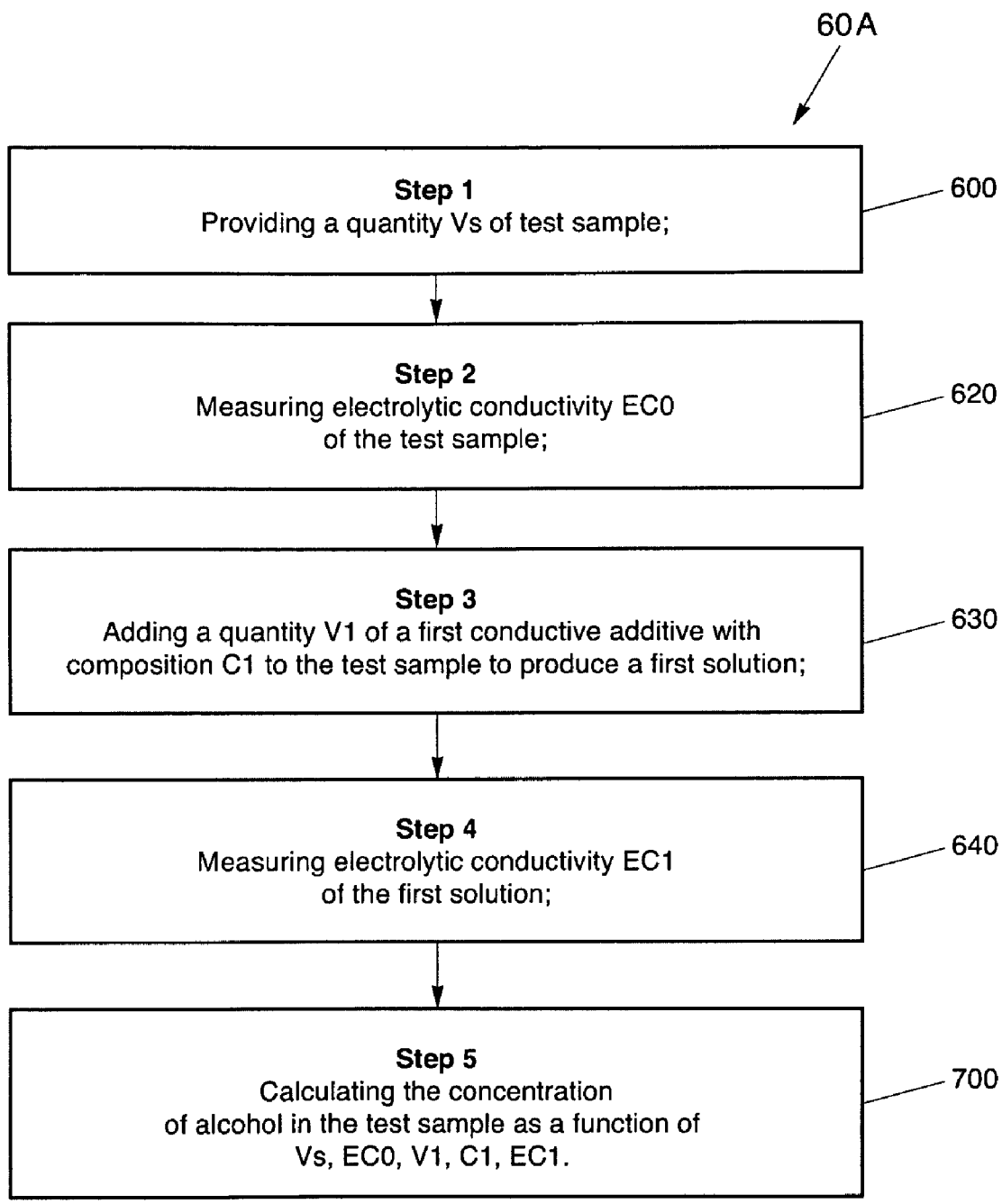
FIG. 5A is a flow chart of another embodiment for the method for alcohol content determination to determine the concentration of alcohol in the test sample.
Figure 5B:
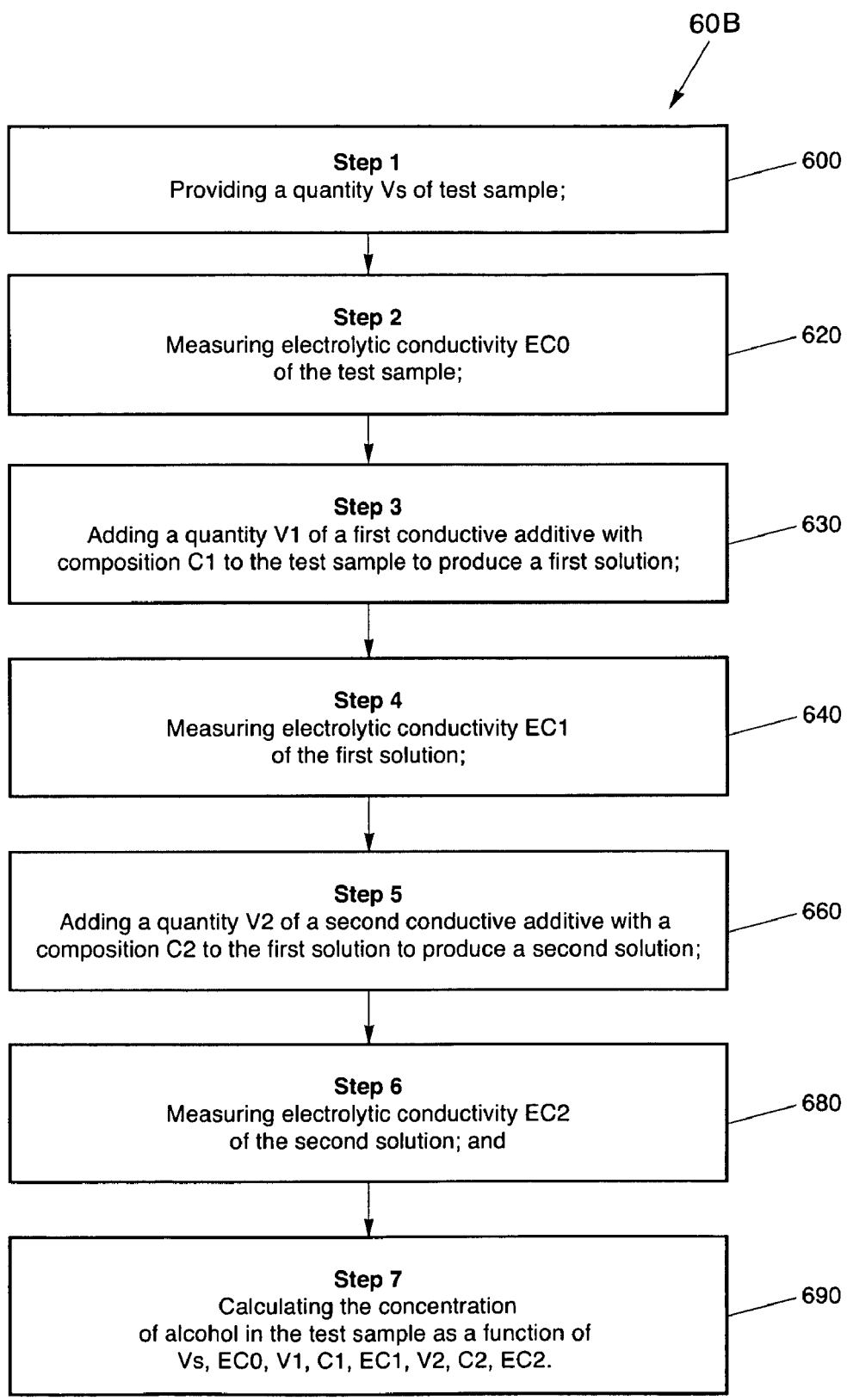
FIG. 5B is a flow chart similar of FIG. 5A that includes a second alcohol concentration to validate the first alcohol concentration.
Figure 5C:
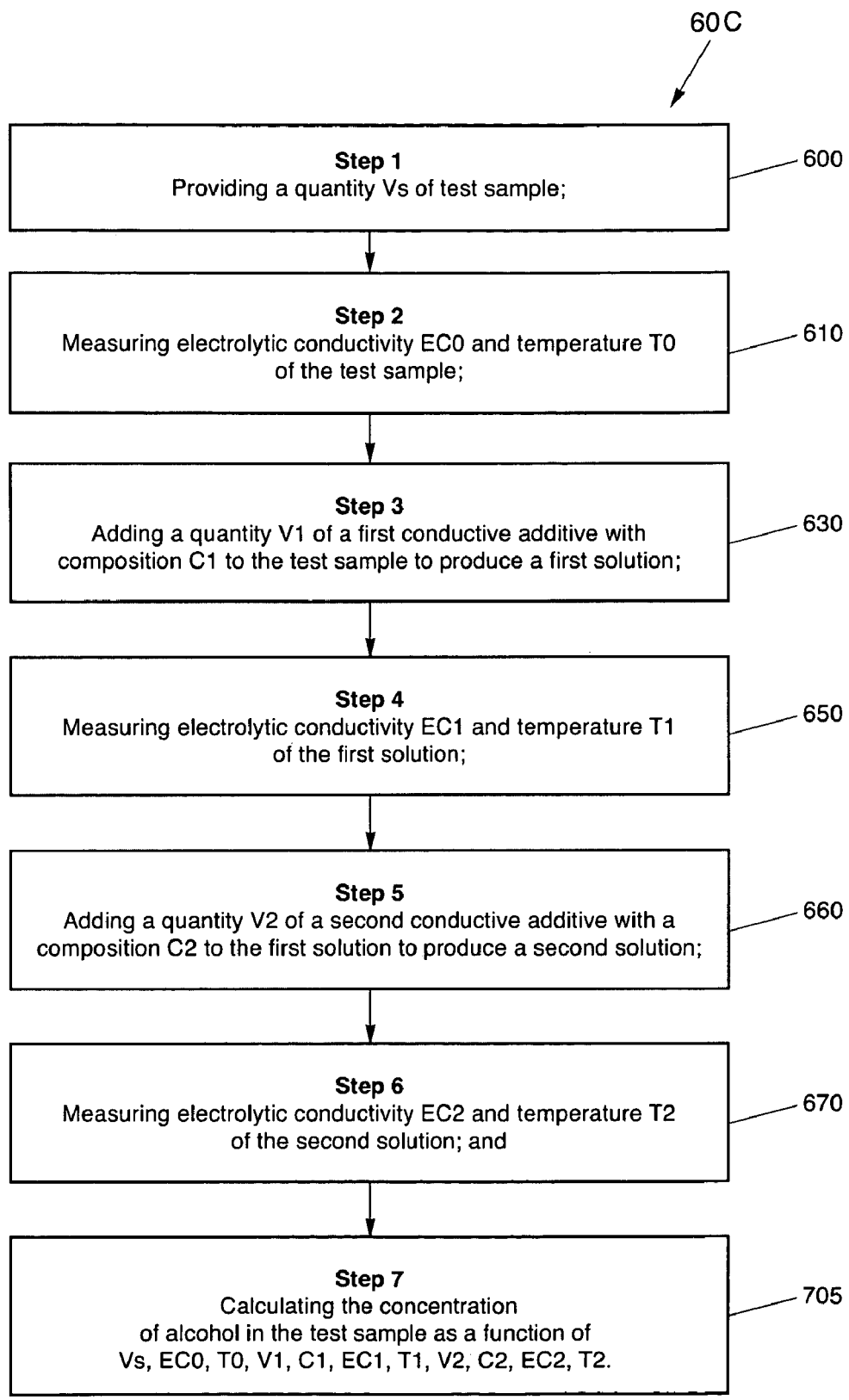
FIG. 5C is a flow chart similar FIG. 5B that includes compensation factors for sugar content and temperature to increase the accuracy of the alcohol concentration.

Now referring to FIGS. 5A-5C, the method for alcohol content determination (60A, 60B, 60C) of a test sample is illustrated in a flow chart. Generally, similar to the method for alcohol content determination 10A-10C, the method 60A-60C measures the change in electrolytic conductivity of a solution as a function of the content of alcohol in the solution and any additions to the solution. As shown in FIGS. 5A-5C, the concentration of alcohol in the test sample is calculated as a function of Vs, EC0, T0, V1, C1, EC1, T1, V2, C2, EC2, T2 in whole or in part. In a preferred embodiment, the algorithm is used in software for operating the apparatus 500. The algorithm will be explained in more detail below.

The method of alcohol content determination 60A, as shown in FIG. 5A, uses five primary steps for performing the method for alcohol content determination by using an alcohol evaluation algorithm. Another embodiment of the method of alcohol content determination 60B, as shown in FIG. 5B, the method 60B includes the five primary steps from method 60A plus it provides additional steps for a second alcohol concentration to validate the first alcohol concentration. In another embodiment of the method of alcohol content determination 60C, as shown in FIG. 5C, the method 60C includes the steps from method 60B plus it provides compensation factors for temperature and sugar to increase the accuracy of the results. It should be noted that the method of the present invention may include more than or fewer than the steps outlined in methods 60A-60C of FIGS. 5A-5C.

For purposes of explanation, the steps for method 60C are discussed below which incorporates the steps outlined in both the method 60A and method 60B. The first step provides a quantity of Vs of test sample 600. The second step of the method measures the electrolytic conductivity EC0 and temperature T0 of the test sample 610. The third step involves adding a quantity V1 of a first conductive additive with composition C1 to the test sample to produce a first solution 630. The fourth step involves measuring electrolytic conductivity EC1 and temperature T1 of the first solution 650. The fifth step involves adding a quantity V2 of a second conductive additive with a composition C2 to the first solution to produce a second solution 660. The sixth step involves measuring electrolytic conductivity EC2 and temperature T2 of the second solution 670.

The steps 1-6 described in the previous paragraph are similar to the steps shown in FIG. 1C of the method 10C but without the graphs. In lieu of the graphs, the concentration of alcohol in the test sample is calculated as a function of Vs, EC0, T0, V1, C1, EC1, T1, V2, C2, EC2, T2 in whole or in part. For the seventh step, to calculate the concentration of alcohol, an alcohol evaluation algorithm may use the following input data (settings and measured values) Vs, EC0, T0, V1, C1, EC1, T1, V2, C2, EC2, T2 705.

The alcohol evaluation algorithm includes the step of alcohol determination solution. In one example, the alcohol content is determined based on the EC0std (25° C.) and EC1std (25° C.) values determined from experimental measurements at 25° C. for standard alcohol (0%, 5%, 10%, 15%, 20%, 25% v/v alcohol) when the initial conductivity is changing (0 mS, 0.5 mS, 1 mS, 1.5 mS, 2 mS, 2.5 mS, 3 mS). From these data, the EC1ref (EC0href) functions are obtained for each alcohol value. EC0 (25° C.) and EC1 (25° C.) are the input data. The 6 EC1 values (5 ranges) are calculated from EC1ref (EC0 (25° C.)) alcohol=ct functions. The input EC1 (25° C.) is searched in the 5 ranges previously determined. The (EC1x, EC1y) range is selected. The alcohol content is obtained from the linear interpolation that use the (EC1x, X %), (EC1y, Y %) and EC1 (25° C.) where EC1x, EC1y are the EC1 values obtained for X % and Y % alcohols.

The alcohol evaluation algorithm is calculated by the following. The EC0 (T0), EC1 (T1) and the dEC1 (according with user settings for sugar compensation) values are the input data in alcohol determination iterative algorithm. The algorithm starts assuming an initial alcohol value of n %. In one example, the EC0 (25° C.) alcohol n and EC1 (25° C.) are obtained using the EC0 (T0) and EC1 (T1) for temperature compensation solution described herein. The EC1 (25° C.) alcohol n is compensated for sugar using the "sugar compensation through alcohol-wine difference factor solution". The alcohol content is evaluated using the "alcohol determination solution" described herein. The determined value is compared with the initial assumed value n %. If the difference is higher than 0.01%, a new iteration is started using the determined alcohol as initial value. If the difference is smaller, the alcohol content is the calculated and the algorithm is stopped.

The alcohol evaluation algorithm which may include steps for sugar compensation through alcohol-wine difference factor solution, temperature compensation, and type of alcohol. The sugar compensation through alcohol-wine difference factor solution includes an evaluation to reach a sugar compensation conclusion. The EC1 difference is between the test samples and the alcohol standard solutions prepared for the same alcohol content. The test samples are grouped by category and the average values of dEC1 differences are determined for each test sample category. The dEC1 compensation for "fixed" sugar content and "type" sugar content are determined using the following factors: the average of the dEC1 values for the test sample categories; "fixed" sugar content; and the average of the dEC1 values for each test sample category. Using the dEC1 average for each test sample category and the average value of sugar content for each test sample category, the dEC1=f (g/L sugar) function is evaluated and it is used for content sugar compensation.

Figure 6:
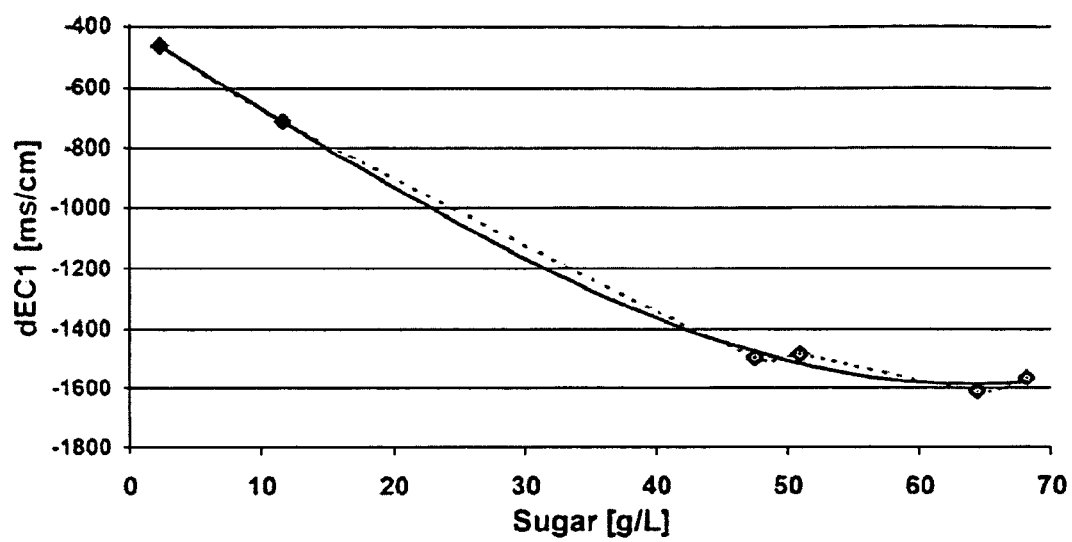
FIG. 6 is a graph which illustrates a correlation between the alcohol-wine difference compensation factor (dEC1) and sugar content.

Now referring to FIG. 6, in one experiment, the graph measures sugar content determination. In this experiment, titration was used to determine sugar content of wine. FIG. 6 shows a correlation between the alcohol wine difference compensation factor (dEC1) and sugar content.

The alcohol evaluation algorithm includes temperature compensation solution. The temperature compensation algorithm compensates the difference in the conductivity measured between T0, T1, and reference temperatures for specified alcohol content. For EC0, measured at T0, the starting point is a temperature variation curve (made for EC0ref at 0, 0.5, 1, 1.5, 2, 2.5, 3 mS/cm and 0%, 5%, 10%, 15%, 20%, 25% v/v alcohol) for each curve the value in the T0 point is calculated. From these values for each alcohol (0% to 25%), the proper interval for the EC0 value is searched. For example, if (X,Y) is an interval, it will be chosen if EC0>X and EC0<=Y. For this interval, the corresponding EC0 values at 25° C. are calculated. As result, the calculated EC0 value is used for each alcohol (0% to 25%). Using the same searching method, the EC0 (25° C.) value is calculated corresponding to the current specified alcohol content. With this value, we can enter the actual alcohol calculation algorithm. For EC1, the algorithm is the same with the observation that we use an EC1 temperature variation curves instead of the EC0 ones. For wine, EC0 (25° C.) alcohol n and EC1 (25° C.) alcohol n values are calculated for use in the alcohol evaluation algorithm.

Figure 7:
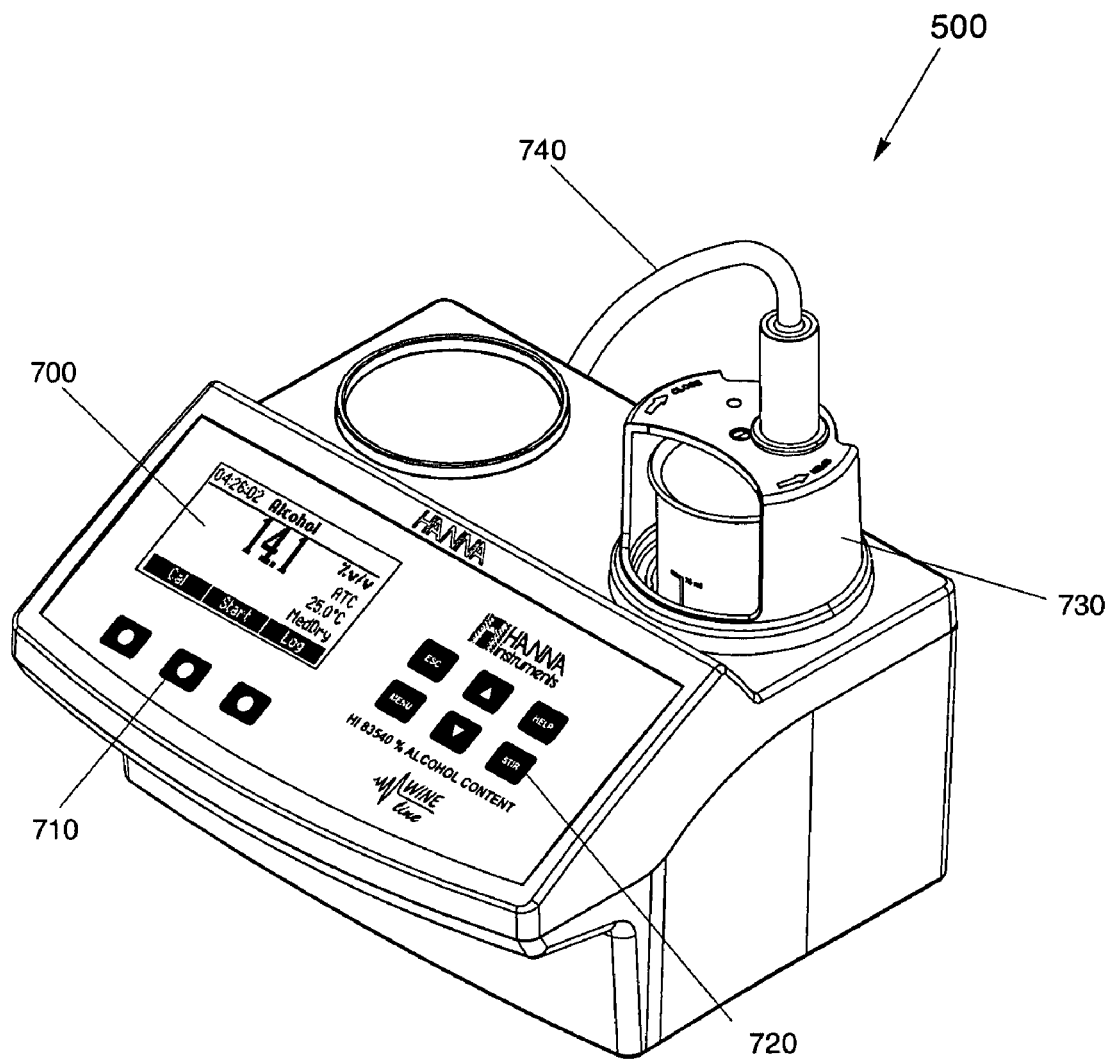
FIG. 7 is a perspective view of an apparatus used for performing the method for alcohol content determination in FIGS. 5A-5C of the present invention.

Now referring to FIG. 7, the method for alcohol content determination 10 is performed using any apparatus or device 500 suitable for measuring alcohol content of a liquid solution. As shown in FIG. 7, the apparatus 500 has a graphic LCD 700, functional keys 710, keypad 720, probe holder 730, and probe 740. In a preferred embodiment, a device 500 is shown in FIG. 7 which may be used to perform the method for alcohol content determination. The apparatus 500 preferably has electrolytic conductivity readings for multiple ranges.

In addition to the apparatus 500, the following materials and devices may be used: conductivity electrode, calibration solution, electrode cleaning solution, stir bar, 100/mL beaker, 60/mL syringe, 30/mL syringe, windows compatible software, solution for alcohol determination.

Figure 8A:
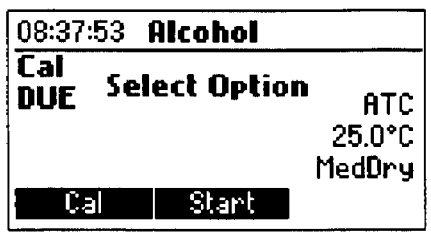
FIGS. 8A-8E are a series of screen shots of the graphic display of the apparatus of FIG. 7 displayed while performing the method for alcohol content determination in FIGS. 1A-1C.
Figure 8B:
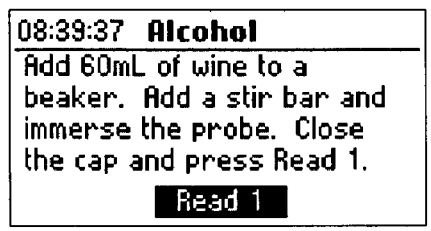
Figure 8C:
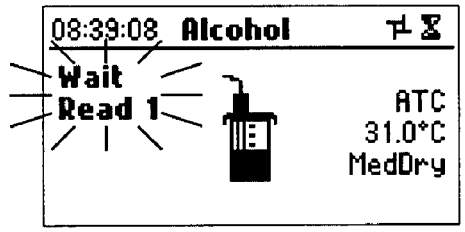

Now referring to FIGS. 8A-8E, as mentioned previously, the apparatus 500 can be used to perform the steps outlined for determining alcohol content. As shown in FIG. 8A, the user starts with the main measure screen. A user presses start to begin a first part of the measurement. As shown in FIG. 8B, the screen prompts the user to add 60 mL of wine or any liquid desired to be measured for alcohol content. After adding the test sample and the conductivity probe, the user must press Read1. As shown in FIG. 8C, the screen indicates the electrode is making a measurement of the sample. If no error message occurs, the screen prompts user to press continue to confirm the sample measurement and proceed to a second part of the analysis of the sample.

Figure 8D:
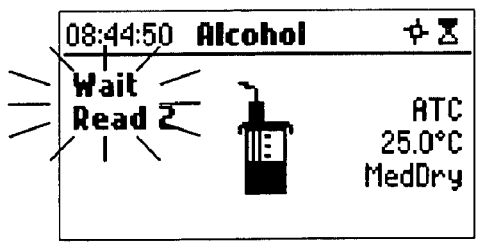
Figure 8E:
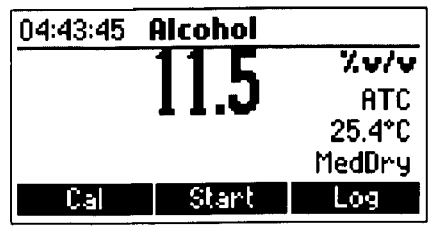

After being prompted to add 30 ml of a first conductive additive, the user must press Read2 to initialize measurement with conductive additive added to the test sample. As shown in FIG. 8D, the screen indicates the conductivity electrode is making a measurement of the sample. As shown in FIG. 8E, the measurement value for alcohol content, expressed as a percentage by volume of the liquid, is displayed.

Figure 9A:
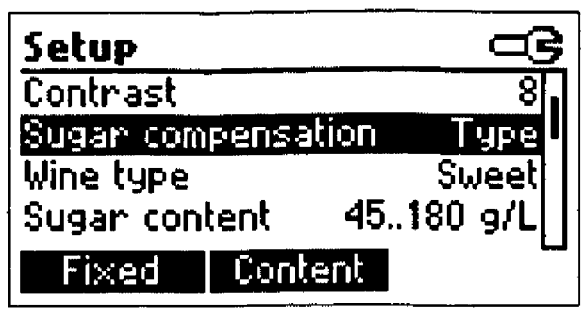
FIGS. 9A-9C are a series of screen shots of the graphic display of the apparatus of FIG. 7 displayed for sugar compensation while performing the method for alcohol content determination in FIGS. 1A-1C.
Figure 9B:
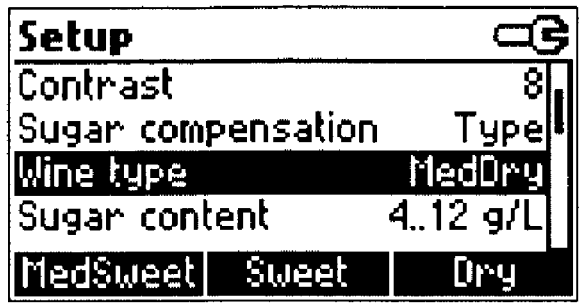
Figure 9C:
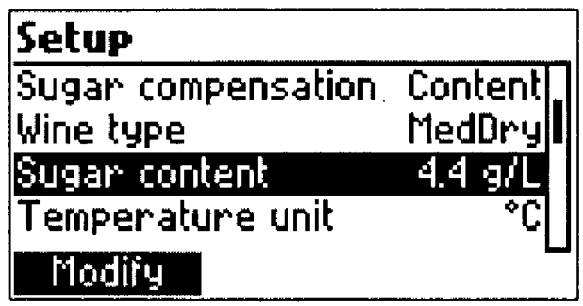
Figure 9C:
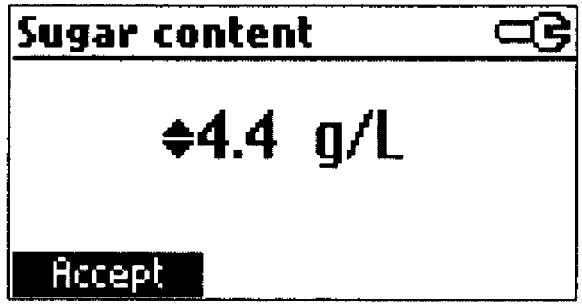

Referring now to FIGS. 9A-9C and 10A-10B, to provide a more accurate measurement using the apparatus 500, a compensation factor is added to the value for alcohol concentration to adjust for additional variables such as sugar content or temperature in the test sample. A shown in FIGS. 9A-9C, the sugar content of the test sample is variable selected from one of the following: fixed, type, or content. When "fixed" is selected, the sugar content is unknown. Fixed is usually selected when the sugar information is not available. For example, in case of dry and medium-dry wines (sugar content less than 12 mg/l). With wine, sugar content over 12 mg/l affects the accuracy of the alcohol content value. When "content" is selected, as shown in FIG. 9C, the amount of sugar in wine is known and inputted accordingly. It should be noted that the compensation factor can be optimized for different classes of alcoholic beverages. In particular, several compensation factors based in the amount of sugar in the beverage and whether this amount is known.

As shown in FIG. 9B, when "type" is selected for sugar compensation, the wine type is known. Wine type is available when type is selected as the sugar compensation method and is used to select the wine type. The options for wine type are: dry, meddry (medium-dry), medsweet (medium-sweet), or sweet. The dry wine has sugar content ranging from 0 to 1.4 g/l. The meddry wine has sugar content ranging from 1.4 to 4.12 g/l. The medsweet wine has sugar content ranging from 4.12 g/l to 12.45 g/l. The sweet wine has sugar content ranging from 12.45 g/l to 45 g/l. Once the user identifies the correct sugar content, as shown in FIG. 9C the user presses "Accept" to confirm the set sugar content.

Figure 10A:
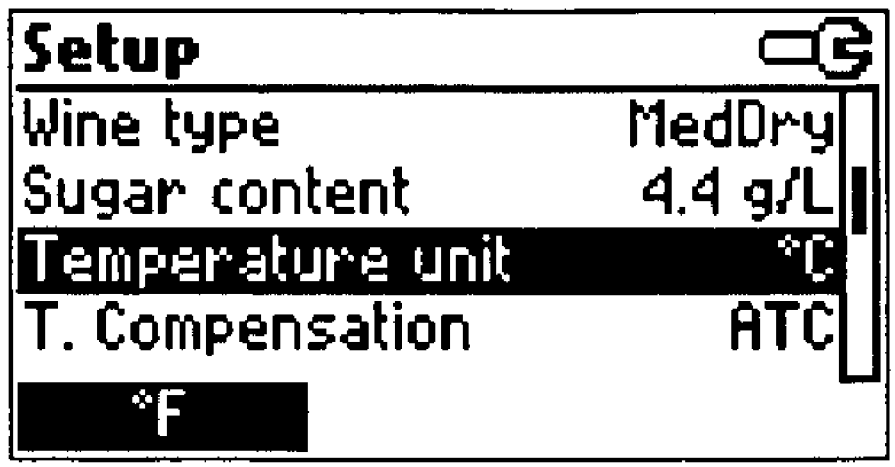
FIGS. 10A-10B are screen shots of the graphic display of the apparatus of FIG. 7 displayed for temperature compensation while performing the method for alcohol content determination in FIGS. 1A-1C.
Figure 10B:
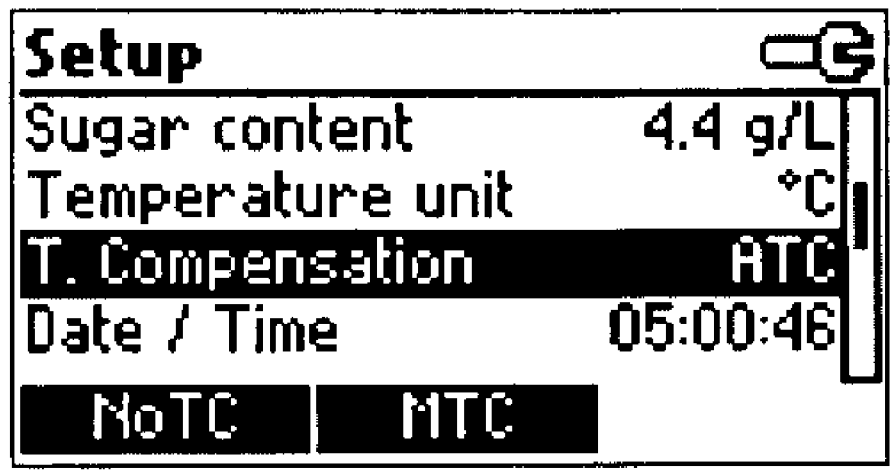

Referring now to FIGS. 10A-10B, another compensation factor is the temperature of the test sample. Temperature is a variable selected from one of the following: ATC, NoTC, or MTC. ATC is selected if automatic temperature compensation is desired. NoTC is selected if no temperature compensation is desired. MTC is selected if manual temperature compensation is desired. Once the temperature and sugar compensation factors are entered, the adjusted value for alcohol content will be displayed on the screen. Note, additional compensation factors may be used to adjust the determination of alcohol content.

In operation, the method for alcohol content determination 10 may be performed on any liquid solution including aqueous solutions, such as wine. To demonstrate the usage of this method, an experiment to determine alcohol content of wine is described herein using the apparatus 500 and related equipment and materials. Please note, the example of using wine with this method by no means limits the application of this method to wine or any specific type of liquid containing alcohol.

For example, in one particular experiment, a user provides 60 mL volume of VS wine sample in a beaker using 60 mL syringe. The conductivity electrode is placed inside the wine sample VS The user measures the electrolytic conductivity value and the temperature value (according with temperature setting 25° C.) if NoTC, user input value for MTC and read value for MTC) of the sample while stirring. The electrolytic conductivity is EC0 at temperature T0.

Next, without changing the position of the measuring system, the user adds 30 mL volume V1 of KCl 0.5M standard using 30 mL syringe. The electrolytic conductivity and temperature values are read (according with temperature compensation setting 25° C. if NoTC, user input value for MTC and read value for ATC). These readings are electrolytic conductivity EC1 at temperature T1.

After the EC0 and EC1 values are obtained, they are temperature compensated to 25° C. (for MTC and ATC modes) using an alcohol evaluation algorithm based on internal EC0 (temperature) and EC1 (temperature) compensation curves determined for standard alcohol references with different initial conductivity values. These values are called EC0 (25° C.) and EC1 (25° C.). Accordingly, with the user setting for sugar compensation at dEC1 correction is applied to the EC1 (25° C.).

As a result, using EC0 (25° C.) and EC1 (25° C.)=EC1 (25° C.)+dEC1 (sugar compensation), the alcohol content for wine is evaluated based upon known data of plotted curves obtained by using different standard alcohol samples with different initial conductivity measured at 25° C. At the end of the measurement, the percentage of alcohol content (% v/v) is displayed on the meter. Of course, actual curves may not be actually plotted as the evaluation preferably may takes place fully within software.

Therefore, the present invention provides a method for alcohol content determination that requires less skill and provides a more accurate result for alcohol content. The present invention provides a method for alcohol content determination of a test sample such as a liquid. Specifically, it provides a low-cost, easy-to-use, and accurate method for determining alcohol content in alcoholic beverages such as wine. The method for alcohol content determination contains the following steps. A known quantity of a test sample, such as wine, is provided. A measurement of electrolytic conductivity (EC0) of the test sample is taken. Next, the known quantity of conductive additive with known composition is added to the test sample to produce a solution. A measurement of electrolytic conductivity (EC1) is taken for the solution. Data, in the form of a graph represents predetermined values on an x axis for EC0 and y axis for EC1 with corresponding curves plotting known alcohol concentrations is provided for comparison. The electrolytic conductivity values for EC0 and EC1 are cross-referenced against the data to determine a value for the alcohol concentration of the test sample.

It should be understood that the method for alcohol content determination describes terms of volume additions as volume/volume. Similarly, the method can be implemented in terms of weights instead of volumes, giving results in (weight/weight) or combinations of weights and volumes.

It would be appreciated by those skilled in the art that various changes and modifications can be made to the illustrated embodiments without departing from the spirit of the present invention. All such modifications and changes are intended to be covered by the appended claims and the present invention.

What is claimed is:

1. A method for alcohol content determination in a test sample, comprising the steps of:
   providing a quantity Vs of a test sample;
   measuring electrolytic conductivity EC0 of the test sample;
   adding a quantity V1 of a first conductive additive with composition C1 to the test sample to produce a first solution;
   measuring electrolytic conductivity EC1 of the first solution;
   providing data representing predetermined values of EC0 and EC1 with corresponding alcohol concentrations associated therewith; and
   cross-referencing electrolytic conductivity values for EC0 and EC1 against the data to determine a first alcohol concentration of the test sample.

2. The method for alcohol content determination of claim 1, wherein the test sample is an alcoholic beverage selected from a group consisting of: wine, beer, and spirits.

3. The method for alcohol content determination of claim 1, wherein the first conductive additive is a conductive salt.

4. The method for alcohol content determination of claim 1, further comprising the step of:
   measuring temperature T0 of the test sample;
   measuring temperature T1 of the first solution;
   providing data representing determined values of T0 and T1; and
   cross-referencing temperature values for T0 and T1 against the data.

5. The method for alcohol content determination of claim 1, further comprising the steps of:
   adding a quantity V2 of a second conductive additive with a composition C2 to the first solution to provide a second solution;
   measuring electrolytic conductivity EC2 of the second solution;
   providing data representing predetermined values of EC0 and EC2 with corresponding alcohol concentrations associated therewith;
   cross-referencing electrolytic conductivity values for EC0 and EC2 against the data to determine a second alcohol concentration of the test sample; and
   comparing the value for the first alcohol concentration against the value for the second alcohol concentration to validate results.

6. The method for alcohol content determination of claim 5, further comprising the step of:
   measuring temperature T0 of the test sample;
   measuring temperature T1 of the first solution;
   measuring temperature T2 of the second solution;
   providing data representing determined values of T0, T1 and T2; and
   cross-referencing temperature values for T0, T1 and T2 against the data.

7. The method for alcohol content determination of claim 1, further comprising the step of:
   adding a compensation factor to the concentration values to adjust for additional variables of the test sample.

8. The method for alcohol content determination of claim 7, wherein the compensation factor is based upon sugar content of the test sample.

9. The method for alcohol content determination of claim 7, wherein the compensation factor is based upon the alcoholic beverage.

10. A method for alcohol content determination in a test sample, comprising the steps of:
    providing a quantity Vs of a test sample;
    measuring electrolytic conductivity EC0 of the test sample;
    adding a quantity V1 of first conductive additive with composition C1 to the test sample to produce a first solution;
    measuring electrolytic conductivity EC1 of the first solution; and
    calculating the concentration of alcohol in the test sample as a function of Vs, EC0, V1, C1, EC1.

11. The method for alcohol content determination of claim 10, wherein an algorithm is used to calculate the concentration of alcohol in the test sample.

12. The method for alcohol content determination of claim 11, wherein the algorithm is used in software for operating an alcohol meter.

13. The method for alcohol content determination of claim 10, wherein the test sample is an alcoholic beverage selected from a group consisting of: wine, beer, and spirits.

14. The method for alcohol content determination of claim 13, further comprising the steps of:
    adding a compensation factor to the concentration values to adjust for additional variables of the test sample.

15. The method for alcohol content determination of claim 14, wherein the compensation factor is based upon sugar content of the test sample.

16. The method for alcohol content determination of claim 14, wherein the compensation factor is based upon the alcoholic beverage.

17. The method for alcohol content determination of claim 10, wherein the first conductive additive is a conductive salt.

18. The method of alcohol content determination of claim 10, further comprising:
    adding a quantity V2 of a second conductive additive with a composition C2 to the first solution to produce a second solution;
    measuring electrolytic conductivity EC2 of the second solution;
    calculating the concentration of alcohol in the test sample as a function of Vs, EC0, V1, C1, EC1, V2, C2, EC2.

19. The method for alcohol content determination of claim 18, further comprising the steps of:
    measuring temperature T0 of the test sample;
    measuring temperature T1 of the first solution;
    measuring temperature T2 of the second solution; and
    calculating the concentration of alcohol in the test sample as a function of Vs, EC0, T0, V1, C1, EC1, T1, V2, C2, EC2, T2.

20. A method for alcohol content determination in a test sample, comprising the steps of:
    providing a quantity Vs of a test sample;
    measuring electrolytic conductivity EC0 of the test sample;
    adding a quantity V1 of first conductive additive with composition C1 to the test sample to produce a first solution;
    measuring electrolytic conductivity EC1 of the first solution;
    adding a quantity V2 of a second conductive additive with a composition C2 to the first solution to produce a second solution;
    measuring electrolytic conductivity EC2 of the second solution; and
    calculating the concentration of alcohol in the test sample as a function of Vs, EC0, V1, C1, EC1, V2, C2, EC2.

21. The method for alcohol content determination of claim 20, wherein an algorithm is used to calculate the concentration of alcohol in the test sample.

22. The method for alcohol content determination of claim 20, wherein the algorithm is used in software for operating an alcohol meter.

23. The method for alcohol content determination of claim 20, wherein the test sample is an alcoholic beverage selected from a group consisting of: wine, beer, and spirits.

24. The method for alcohol content determination of claim 23, further comprising the steps of:
adding a compensation factor to the concentration values to adjust for additional variables of the test sample.

25. The method for alcohol content determination of claim 24, wherein the compensation factor is based upon sugar content of the test sample.

26. The method for alcohol content determination of claim 24, wherein the compensation factor is based upon the alcoholic beverage.

27. The method for alcohol content determination of claim 20, wherein the first conductive additive is a conductive salt.

28. The method for alcohol content determination of claim 20, further comprising the steps of:
measuring temperature T0 of the test sample;
measuring temperature T1 of the first solution;
measuring temperature T2 of the second solution; and
calculating the concentration of alcohol in the test sample as a function of Vs, EC0, T0, V1, C1, EC1, T1, V2, C2, EC2, T2.

29. An apparatus for determining alcohol content in a test sample, comprising:
a means for determining alcohol content in a test sample comprising the following steps:
providing a quantity Vs of a test sample;
measuring electrolytic conductivity EC0 of the test sample;
adding a quantity V1 of first conductive additive with composition C1 to the test sample to produce a first solution;
measuring electrolytic conductivity EC1 of the first solution; and
calculating the concentration of alcohol in the test sample as a function of Vs, EC0, V1, C1, EC1.

* * * * *